United States Patent
Chassagne et al.

(10) Patent No.: US 11,312,741 B2
(45) Date of Patent: Apr. 26, 2022

(54) SEPARATION OF OLIGOSACCHARIDES FROM FERMENTATION BROTH

(71) Applicant: GLYCOM A/S, Hørsholm (DK)

(72) Inventors: Pierre Chassagne, Beaumont (FR); Nikolay Khanzhin, Humlebæk (DK); Martin Matwiejuk, Hamburg (DE); Markus Jondelius Hederos, Trelleborg (SE); Niels Banke, Søborg (DK)

(73) Assignee: GLYCOM A/S, Hørsholm (DK)

( * ) Notice: Subject to any disclaimer, the term of this patent is extended or adjusted under 35 U.S.C. 154(b) by 598 days.

(21) Appl. No.: 16/094,508

(22) PCT Filed: Apr. 19, 2017

(86) PCT No.: PCT/IB2017/052252
§ 371 (c)(1),
(2) Date: Oct. 18, 2018

(87) PCT Pub. No.: WO2017/182965
PCT Pub. Date: Oct. 26, 2017

(65) Prior Publication Data
US 2019/0119314 A1    Apr. 25, 2019

(30) Foreign Application Priority Data

Apr. 19, 2016 (EP) .................... 16165961
Jun. 24, 2016 (EP) .................... 16176257
Jun. 24, 2016 (EP) .................... 16176285

(51) Int. Cl.
| C07H 13/04 | (2006.01) |
| B01D 61/02 | (2006.01) |
| B01D 61/14 | (2006.01) |
| B01D 61/58 | (2006.01) |
| C07H 1/06 | (2006.01) |
| C12P 19/28 | (2006.01) |
| B01D 15/36 | (2006.01) |
| B01J 41/07 | (2017.01) |
| B01D 61/16 | (2006.01) |
| B01J 39/05 | (2017.01) |
| B01D 15/18 | (2006.01) |
| B01J 20/20 | (2006.01) |
| G01N 30/96 | (2006.01) |
(Continued)

(52) U.S. Cl.
CPC ......... *C07H 13/04* (2013.01); *B01D 15/1871* (2013.01); *B01D 15/362* (2013.01); *B01D 15/363* (2013.01); *B01D 61/02* (2013.01); *B01D 61/027* (2013.01); *B01D 61/14* (2013.01); *B01D 61/145* (2013.01); *B01D 61/16* (2013.01); *B01D 61/58* (2013.01); *B01J 20/20* (2013.01); *B01J 39/05* (2017.01); *B01J 41/07* (2017.01); *C07H 1/06* (2013.01); *C12P 19/28* (2013.01); *G01N 30/96* (2013.01);

*B01D 2311/2623* (2013.01); *B01D 2311/2688* (2013.01); *C12P 19/26* (2013.01); *C12Y 204/01149* (2013.01); *G01N 30/02* (2013.01)

(58) Field of Classification Search
CPC .......... C07H 13/04; C07H 1/06; B01D 61/02; B01D 61/14; B01D 15/363; B01D 15/362; B01D 61/16; B01D 15/1871; B01D 61/027; B01D 61/145; B01D 61/58; B01D 2311/2623; B01D 2311/2688; B01D 15/361; B01J 41/07; B01J 39/05; B01J 20/20; G01N 30/96; G01N 30/02; C12P 19/28; C12P 19/26; C12Y 204/01149
See application file for complete search history.

(56) References Cited

U.S. PATENT DOCUMENTS

2016/0199784 A1* 7/2016 Choudhary ............. A23J 1/205
424/535
2016/0333042 A1* 11/2016 Jennewein ............. A23L 33/40
(Continued)

FOREIGN PATENT DOCUMENTS

| EP | 1911850 A1 | 4/2008 |
| EP | 2722394 A1 | 4/2014 |
| EP | 2896628 A1 | 7/2015 |
(Continued)

OTHER PUBLICATIONS

Rosane Rosa de Souza, et.al, Recovery and purification of lactose from whey, Chemical Engineering and Processing: Process Intensification, vol. 49, Issue 11, 2010, pp. 1137-1143, https://doi.org/10.1016/j.cep.2010.08.015. (Year: 2010).*
(Continued)

*Primary Examiner* — Bradley R Spies
*Assistant Examiner* — Jeannie McDermott
(74) *Attorney, Agent, or Firm* — Neal, Gerber & Eisenberg LLP

(57) ABSTRACT

The invention relates to a method for obtaining an N-acetyl-glucosamine containing neutral oligosaccharide from a fermentation broth, wherein said oligosaccharide is produced by culturing a genetically modified microorganism capable of producing said oligosaccharide from an internalized carbohydrate precursor, comprising the steps of: i) ultrafiltration (UF), preferably to separate biomass from the broth, ii) nanofiltration (NF), preferably to concentrate said oligosaccharide in the broth and/or reduce an inorganic salt content of the broth, and iii) treating the broth with an ion exchange resin, preferably to remove charged materials, and/or subjecting the broth to chromatography, preferably to remove hydrophobic impurities.

8 Claims, No Drawings

(51) Int. Cl.
*C12P 19/26* (2006.01)
*G01N 30/02* (2006.01)

(56) References Cited

U.S. PATENT DOCUMENTS

| | | | |
|---|---|---|---|
| 2019/0175631 A1* | 6/2019 | Khanzhin | C07H 1/00 |
| 2019/0320672 A1* | 10/2019 | Holst | A23C 9/144 |

FOREIGN PATENT DOCUMENTS

| | | |
|---|---|---|
| WO | 9502683 | 7/1994 |
| WO | 9815581 | 4/1998 |
| WO | 0104341 A1 | 1/2001 |
| WO | 2005039299 A2 | 5/2005 |
| WO | 2012034996 A1 | 3/2012 |
| WO | 2012112777 A2 | 8/2012 |
| WO | 2013136280 A1 | 9/2013 |
| WO | 2013182206 A1 | 12/2013 |
| WO | 2014048439 A1 | 4/2014 |
| WO | 2014086373 A1 | 6/2014 |
| WO | 2014153253 A1 | 9/2014 |
| WO | 2015032413 A1 | 3/2015 |
| WO | 2015036138 A1 | 3/2015 |
| WO | 2015049331 A1 | 4/2015 |
| WO | 2015150328 A1 | 10/2015 |
| WO | 2015188834 A1 | 12/2015 |
| WO | 2015197082 A1 | 12/2015 |
| WO | 2016008602 A1 | 1/2016 |
| WO | 2016040531 A1 | 3/2016 |

OTHER PUBLICATIONS

Baumgärtner, F., et al., "Galactose-limited fed-batch cultivation of *Escherichia coli* for the production of lacto-N-tetraose," Enzyme and Microbial Technology, 2015, vol. 75-76, pp. 37-43.

Baumgärtner, F., et al., "Synthesis of the Human Milk Oligosaccharide Lacto-N-Tetraose in Metabolically Engineered, Plasmid-Free *E. coli*," ChemBioChem, 2014, vol. 15, 1896-1900.

Bettler, E., et al., "The living factory: In vivo production of N-acetyllactosamine containing carbohydrates in *E. coli*," Glycoconjugate Journal, 1999, vol. 16, pp. 205-212.

Cottaz, S., et al., "Genetic engineering of *Escherichia coli* for the production of NI,NII-diacetylchitobiose (chitinbiose) and its utilization as a primer for the synthesis of complex carbohydrates," Metabolic Engineering, 2005, vol. 7, pp. 311-317.

Dumon, C., et al., "Assessment of the Two Helicobacter pylori r-1,3-Fucosyltransferase Ortholog Genes for the Large-Scale Synthesis of LewisX Human Milk Oligosaccharides by Metabolically Engineered *Escherichia coli*," Biotechnol. Prog. vol. 20, 2004, pp. 412-419.

Dumon, C., et al., "In vivo fucosylation of lacto-N-neotetraose and lacto-N-neohexaose by heterologous expression of Helicobacter pylori a-1,3 fucosyltransferase in engineered *Escherichia coli*," Glycoconjugate Journal, 2001, vol. 18, pp. 465-474.

Fort, S., et al., Biosynthesis of conjugatable saccharidic moieties of GM2 and GM3 gangliosides by engineered *E. coli*, ChemComm, 2005, 0, pp. 2558-2560. DOI: 10 1039/b500686d.

Gebus, C., et al., "Synthesis of a-galactosyl epitopes by metabolically engineered *Escherichia coli*," Carbohydrate Research, 2012, vol. 361, pp. 83-90.

Han, N.S., et al., "Biotechnological production of human milk oligosaccharides," Biotechnology Advances, 2012, vol. 30, pp. 1268-1278.

Murata, T., et al., "Facile enzymatic conversion of lactose into lacto-N-tetraose and lacto-N-neotetraose," Glycoconjugate Journal, 1999, vol. 16, pp. 189-195.

Priem, B., et al., "A new fermentation process allows large-scale production of human milk oligosaccharides by metabolically engineered bacteria," Glycobiology, 2002, vol. 12(4), pp. 235-240.

Samain, E., et al., "Gram-scale synthesis of recombinant chitooligosaccharides in *Escherichia coli*," Carbohydrate Research, 1997, vol. 302, pp. 35-42.

Samain, E., et al., "Production of O-acetylated and sulfated chitooligosaccharides by recombinant *Escherichia coli* strains harboring different combinations of nod genes," Journal of Biotechnology, 1999, vol. 72, pp. 33-47.

Urashima, T. et al. (2011) Nutrition and Diet Research Progress: Milk Oligosaccharides. New fork: Nova Science Publishers, Inc, 92 pages.

* cited by examiner

SEPARATION OF OLIGOSACCHARIDES FROM FERMENTATION BROTH

CROSS-REFERENCE TO RELATED APPLICATION

This application is a national stage entry pursuant to 35 U.S.C. § 371 of International Application No. PCT/IB2017/052252 filed on Apr. 19, 2017 which claims priority to European Patent Application No. 16176285.1 filed on Jun. 24, 2016, European Patent Application No. 16176257.0 filed on Jun. 24, 2016, and European Patent Application No. 16165961.0 filed on Apr. 19, 2016, the contents of all of which are fully incorporated herein by reference.

FIELD OF THE INVENTION

The present invention relates to the isolation and separation of N-acetylglucosamine containing neutral oligosaccharides from the fermentation broth in which they are produced by a recombinant microorganism.

BACKGROUND OF THE INVENTION

During the past decades, the interest in the preparation and commercialisation of human milk oligosaccharides (HMOs) has been increasing steadily. The importance of HMOs is directly linked to their unique biological activities, therefore HMOs have become important potential products for nutrition and therapeutic uses. As a result, low cost ways of producing industrially HMOs have been sought.

To date, the structures of at least 115 HMOs have been determined (see Urashima et al.: *Milk Oligosaccharides*, Nova Biomedical Books, New York, 2011, ISBN: 978-1-61122-831-1), and considerably more are probably present in human milk. The HMOs comprise a lactose (Galβ1-4Glc) moiety at the reducing end and may be elongated with an N-acetylglucosamine, or one or more N-acetyllactosamine moiety/moieties (Galβ1-4GlcNAc) and/or a lacto-N-biose moiety (Galβ1-3GlcNAc). The N-acetylglucosamine containing core structures identified to date, for the 115 HMOs, are listed in Table 1. Lactose and the N-acetyllactosaminylated or lacto-N-biosylated core derivatives may further be substituted with one or more fucose and/or sialic acid residue(s), or lactose may be substituted with an additional galactose, to give HMOs known so far.

TABLE 1

N-acetylglucosamine containing core HMO structures

| No | Core name | Core structure |
|---|---|---|
| 1 | lacto-N-triose II (LNTri II) | GlcNAcβ1-3Galβ1-4Glc |
| 2 | lacto-N-tetraose (LNT) | Galβ1-3GlcNAcβ1-3Galβ1-4Glc |
| 3 | lacto-N-neotetraose (LNnT) | Galβ1-4GlcNAcβ1-3Galβ1-4Glc |
| 4 | lacto-N-hexaose (LNH) | Galβ1-3GlcNAcβ1-3(Galβ1-4GlcNAcβ1-6)Galβ1-4Glc |
| 5 | lacto-N-neohexaose (LNnH) | Galβ1-4GlcNAcβ1-3(Galβ1-4GlcNAcβ1-6)Galβ1-4Glc |
| 6 | para-lacto-N-hexaose (pLNH) | Galβ1-3GlcNAcβ1-3Galβ1-4GlcNAcβ1-3Galβ1-4Glc |
| 7 | para-lacto-N-neohexaose (pLNnH) | Galβ1-4GlcNAcβ1-3Galβ1-4GlcNAcβ1-3Galβ1-4Glc |
| 8 | lacto-N-octaose (LNO) | Galβ1-3GlcNAcβ1-3(Galβ1-4GlcNAcβ1-3Galβ1-4GlcNAcβ1-6)Galβ1-4Glc |
| 9 | lacto-N-neooctaose (LNnO) | Galβ1-4GlcNAcβ1-3(Galβ1-3GlcNAcβ1-3Galβ1-4GlcNAcβ1-6)Galβ1-4Glc |
| 10 | iso-lacto-N-octaose (iLNO) | Galβ1-3GlcNAcβ1-3(Galβ1-3GlcNAcβ1-3Galβ1-4GlcNAcβ1-6)Galβ1-4Glc |
| 11 | para-lacto-N-octaose (pLNO) | Galβ1-3GlcNAcβ1-3Galβ1-4GlcNAcβ1-3Galβ1-4GlcNAcβ1-3Galβ1-4Glc |
| 12 | lacto-N-neodecaose (LNnD) | Galβ1-3GlcNAcβ1-3[Galβ1-4GlcNAcβ1-3(Galβ1-4GlcNAcβ1-6)Galβ1-4GlcNAcβ1-6]Galβ1-4Glc |
| 13 | lacto-N-decaose (LND) | Galβ1-3GlcNAcβ1-3[Galβ1-3GlcNAcβ1-3(Galβ1-4GlcNAcβ1-6)Galβ1-4GlcNAcβ1-6]Galβ1-4Glc |

Direct fermentative production of HMOs, especially of short chain trisaccharides, has recently become practical (Han et al. *Biotechnol. Adv.* 30, 1268 (2012) and references cited therein). Such fermentation technology has used a recombinant *E. coli* system wherein one or more types of glycosyl transferases originating from viruses or bacteria have been co-expressed to glycosylate exogenously added lactose, which has been internalized by the LacY permease of the *E. coli*. However, the use of more than one type of glycosyl transferase to produce oligosaccharides of four or more monosaccharide units, like LNT, LNnT or their fucosylated derivatives, has always led to the formation of a complex mixture of oligosaccharides. This is believed to have been due to either an ineffective second glycosylation or the overglycosylation of the diverse intermediates produced from the lactose feed as a consequence of varying enzymatic activity of the different glycosyl transferases (WO 01/04341, Dumon et al. *Glycoconj. J.* 18, 465 (2001), Priem et al. *Glycobiology* 12, 235 (2002), Dumon et al. *Biotechnol. Prog.* 20, 412 (2004), Gebus et al. *Carbohydr. Res.* 361, 83 (2012), Baumgärtner et al. *ChemBioChem* 15, 1896 (2014) and *Enzyme Microb. Technol.* 75-76, 37 (2015), WO 2014/153253, WO 2015/036138, WO 2016/008602, WO 2016/040531).

For separating LNnT or LNT from carbohydrate by-products, active charcoal treatment combined with gel filtration chromatography has been proposed as a method of choice (for LNnT: WO 01/04341, Dumon et al. *Glycoconj. J.* 18, 465 (2001), Priem et al. *Glycobiology* 12, 235 (2002), Gebus et al. *Carbohydr. Res.* 361, 83 (2012); for LNT: Baumgärtner et al. *ChemBioChem* 15, 1896 (2014)). Although gel filtration chromatography is a convenient lab scale method, it cannot be efficiently scaled up for industrial production. Recently, WO 2015/049331 has disclosed the following operation sequence to purify LNT after bacterial fermentation: to provide a clear particle free solution, electrodialysis, nanofiltration, first simulated moving bed strong cation exchange resin chromatography, electrodialysis, ultrafiltration, second simulated moving bed strong cation exchange resin chromatography. Other prior art, EP-A-2896628, has described a process for purification of 2'-FL from a fermentation broth obtained by microbial fermentation comprising the following steps: ultrafiltration, strong cation exchange resin chromatography ($H^+$-form), neutralization, strong anion exchange resin chromatography ($Cl^-$-form), neutralization, nanofiltration/diafiltration, active charcoal treatment, electrodialysis, strong cation exchange resin chromatography ($Na^+$-form), strong anion exchange resin chromatography ($Cl^-$-form), active charcoal treatment, electrodialysis.

However, the above procedures are rather complex and expensive.

Alternative, more efficient and robust procedures for isolating and purifying LNT, LNnT and other N-acetylglucosamine containing HMOs from non-carbohydrate components of the fermentation broth in which they are produced on an industrial scale are needed.

SUMMARY OF THE INVENTION

The invention relates to a method for obtaining an N-acetylglucosamine containing neutral oligosaccharide from a fermentation broth, wherein said oligosaccharide is produced by culturing a genetically modified microorganism capable of producing said oligosaccharide from an internalized carbohydrate precursor, comprising the steps of:
  i) ultrafiltration (UF), preferably to separate biomass from the broth,
  ii) nanofiltration (NF), preferably to concentrate said oligosaccharide in the broth and/or reduce an inorganic salt content of the broth, and
  iii) treating the broth with an ion exchange resin, preferably to remove charged materials, and/or subjecting the broth to chromatography, preferably to remove hydrophobic impurities.

According to an embodiment of the invention, step i) is performed before any of the steps ii) and iii).

According to another embodiment of the invention, the N-acetylglucosamine containing neutral oligosaccharide is an N-acetylglucosamine containing neutral HMO, preferably an N-acetylglucosamine containing core HMO.

Certain embodiments of the invention comprise one or more further optional steps, such as activated charcoal treatment (preferably to decolorize the broth) and/or crystallization of the N-acetylglucosamine containing neutral oligosaccharide. Preferably, the further optional step is not electrodialysis.

The invention relates, in another aspect, to the separation of an N-acetylglucosamine containing neutral oligosaccharide from dissolved inorganic and organic salts, acids and bases in an aqueous medium from a fermentation or enzymatic process, comprising the step of treating said aqueous medium with a strong cation exchange resin in $H^+$-form and a weak anion exchange resin in free base form.

DETAILED DESCRIPTION OF THE INVENTION

1. Terms and Definitions

In accordance with this invention, the term "N-acetylglucosamine containing neutral oligosaccharide" preferably means a sugar polymer containing at least two monosaccharide units, at least one of which is an N-acetylglucosamine moiety. The N-acetylglucosamine containing neutral oligosaccharide does not comprise an acidic monosaccharide unit such as aldonic acid, keto-aldonic acid (such as sialic acid), aldaric acid, alduronic acid or a basic monosaccharide moiety such as one with free amino group. The N-acetylglucosamine containing neutral oligosaccharide can have a linear or branched structure containing monosaccharide units that are linked to each other by interglycosidic linkage. Advantageously, the N-acetylglucosamine containing neutral oligosaccharide is at least a trisaccharide in which an N-acetylglucosamine is attached to a lactose moiety via its galactose. More advantageously, the N-acetylglucosamine containing neutral oligosaccharide is an N-acetylglucosamine containing neutral human milk oligosaccharide.

The term "N-acetylglucosamine containing neutral human milk oligosaccharide" preferably means a non-sialylated (therefore neutral) complex carbohydrate found in human breast milk (Urashima et al.: *Milk Oligosaccharides*. Nova Biomedical Books, New York, 2011, ISBN: 978-1-61122-831-1) comprising a core structure being a lactose unit at the reducing end that is elongated, via its 3'-OH group, by an N-acetylglucosamine, an N-acetyllactosamine (Galβ1-4GlcNAc) or a lacto-N-biose moiety (Galβ1-3GlcNAc); the N-acetyllactosamine and the lacto-N-biose containing derivatives can optionally be substituted by one or more α-L-fucopyranosyl moieties. Examples of such HMOs include lacto-N-triose II, LNT, LNnT LNFP I, LNFP II, LNFP III, LNFP V, LNDFH I, LNDFH II, LNDFH III, LNH, pLNH, LNnH, pLNnH, etc.

The term "N-acetylglucosamine containing core human milk oligosaccharide" preferably means an N-acetylglucosamine containing neutral human milk oligosaccharide (see above) that lacks any fucose residue. The preferred N-acetylglucosamine containing core HMOs are listed in Table 1.

The term "genetically modified cell" or "genetically modified microorganism" preferably means a cell of a microorganism, such as a bacterial or fungi cell, e.g. an *E. coli* cell, which has been genetically manipulated to include at least one alteration in its DNA sequence. The term "at least one genetic alteration" means a genetic alteration that can result in a change in the original characteristics of the wild type cell, e.g. the modified cell is able to perform additional chemical transformation due to the introduced new genetic material that encodes the expression of an enzymes not being in the wild type cell, or is not able to carry out transformation like degradation due to removal of gene/genes (knockout). A genetically modified cell can be produced in a conventional manner by genetic engineering techniques that are well-known to those skilled in the art.

The term "genetically modified microorganism capable of producing an N-acetylglucosamine containing neutral oligosaccharide from an internalized carbohydrate precursor" preferably means a cell of a microorganism, such as a bacterium or yeast, preferably a bacterium, which is genetically manipulated (vide supra) to comprise a recombinant gene encoding an N-acetylglucosaminyl transferase necessary for the synthesis of said N-acetylglucosamine containing neutral oligosaccharide, a biosynthetic pathway to produce a GlcNAc nucleotide donor suitable to be transferred by said glycosyl transferase to a carbohydrate precursor (acceptor) and a mechanism of internalization of a carbohydrate precursor (acceptor) from the culture medium into the cell where it is N-acetylglucosaminylated to produce the N-acetylglucosamine containing neutral oligosaccharide of interest.

The term "biomass", in the context of fermentation, refers to the suspended, precipitated or insoluble materials originating from fermentation cells, like intact cells, disrupted cells, cell fragments, proteins, protein fragments, polysaccharides. The term "biomass", in the context of enzymatic reaction, refers to (mainly denatured and/or precipitated) proteins or protein fragments originating from the enzyme used. The biomass can be separated from the supernatant or the reaction mixture by e.g. centifugation or ultrafiltration.

The term "Brix" refers to degrees Brix, that is the sugar content of an aqueous solution (g of sugar in 100 g of solution). In this regard, Brix of the N-acetylglucosamine containing neutral oligosaccharide solution of this application refers to the overall carbohydrate content of the solution including the N-acetylglucosamine containing neutral oligosaccharide and its accompanying carbohydrates. Brix is measured by a calibrated refractometer.

2. Method for Separating N-Acetylglucosamine Containing Neutral Oligosaccharides from the Fermentation Broth 2.1. Production of the N-Acetylglucosamine Containing Neutral Oligosaccharide by a Genetically Modified Microorganism The production of the N-acetylglucosamine containing neutral oligosaccharide by culturing a genetically modified cell is preferably performed as the following.

An exogenously added acceptor is internalized from the culture medium into the cell where it is converted to the N-acetylglucosamine containing neutral oligosaccharide of interest in a reaction comprising enzymatic glycosylation. In one embodiment, the internalization can take place via a passive transport mechanism during which the exogenous acceptor diffuses passively across the plasma membrane of the cell. The flow is directed by the concentration difference in the extra- and intracellular space with respect to the acceptor molecule to be internalized, which acceptor is supposed to pass from the place of higher concentration to the zone of lower concentration tending towards equilibrium. In another embodiment, the exogenous acceptor can be internalized in the cell with the aid of an active transport mechanism, during which the exogenous acceptor diffuses across the plasma membrane of the cell under the influence of a transporter protein or permease of the cell. Lactose permease (LacY) has specificity towards mono- or disaccharide selected from galactose, N-acetyl-glucosamine, a galactosylated monosaccharide (such as lactose), an N-acetyl-glucosaminylated monosaccharide and glycosidic derivatives thereof. All these carbohydrate derivatives can be easily taken up by a cell expressing a LacY permease (such a cell is also referred herein to as a LacY phenotype cell) by means of an active transport and accumulate in the cell before being glycosylated (WO 01/04341, Fort et al. *J. Chem. Soc., Chem. Comm.* 2558 (2005), EP-A-1911850, WO 2013/182206, WO 2014/048439). The specificity towards the sugar moiety of the substrate to be internalized can be altered, e.g. by mutation using well-known recombinant DNA techniques. Preferably, the cell expressing a lacY gene encoding the lactose permease lacks enzymes or at least has a reduced activity of enzymes that are able to degrade the internalized acceptors. Preferably, the cell lacks β 1,4-galactosidase or at least has a reduced activity of β 1,4-galactosidase encoded by the lacZ gene (such a cell is also referred herein to as a LacZ$^-$ phenotype cell).

In one preferred embodiment, the exogenously added acceptor is lactose, and its internalization takes place via an active transport mechanism mediated by a lactose permease of the cell, more preferably LacY.

Being internalized into the cell, the acceptor is glycosylated by means of one or more glycosyl transferases, one of which is an N-acetylglucosaminyl transferase, expressed by a heterologous gene or nucleic acid sequence which is introduced into the cell by known techniques, e.g. by integrating it into the chromosome of the cell or using an expression vector. The genetically modified cell normally comprises a biosynthetic pathway to produce one or more monosaccharide nucleotide donors, one of which is UDP-GlcNAc, suitable to be transferred by the corresponding glycosyl transferase. Most of the microorganisms are able to produce UDP-GlcNAc via their natural central carbon metabolism.

An N-acetylglucosamine containing neutral oligosaccharide can be produced by a genetically modified microorganism in accordance with e.g. Samain et. al. *Carbohydr. Res.* 302, 35 (1997), Bettler et al. *Glycoconj. J.* 16, 205 (1999), Dumon et al. *Glycoconj. J.* 18, 465 (2001), Priem et al. *Glycobiology* 12, 235 (2002), Dumon et al. *Biotechnol. Prog.* 20, 412 (2004), Cottaz et al. *Metab. Eng.* 7, 311 (2005), Gebus et al. *Carbohydr. Res.* 361, 83 (2012), Baumgärtner et al. *ChemBioChem* 15, 1896 (2014) and *Enzyme Microb. Technol.* 75-76, 37 (2015), WO 01/04341, WO 2014/153253, WO 2015/036138, WO 2015/150328, WO 2015/197082, WO 2016/008602, WO 2016/040531 or EP-A-2722394.

In preferred embodiments, the genetically modified microorganism is *E. coli*.

In one preferred embodiment, the N-acetylglucosamine containing neutral oligosaccharide is an N-acetylglucosamine containing neutral HMO, more preferably an N-acetylglucosamine containing core HMO, particularly lacto-N-triose II, LNT or LNnT.

Accordingly, in a preferred embodiment, the process is designed for producing lacto-N-triose II, LNT or LNnT. This production process, preferably, comprises the following steps:

a) providing a genetically modified *E. coli* cell of LacY$^+$ phenotype or LacZ$^-$, LacY$^+$ phenotype, wherein said cell comprises:
   a recombinant gene encoding a β-1,3-N-acetyl-glucosaminyl transferase enzyme which is able to transfer the GlcNAc of UDP-GlcNAc to the internalized lactose,
   optionally a recombinant gene encoding a β-1,3- or a β-1,4-galactosyl transferase enzyme which is able to transfer the galactosyl residue of UDP-Gal to the N-acetyl-glucosaminylated lactose, and
   one or more genes encoding a biosynthetic pathway to UDP-GlcNAc and optionally to UDP-Gal,
b) culturing the genetically modified *E. coli* cell of LacY$^+$ phenotype or LacZ$^-$, LacY$^+$ phenotype in the presence of exogenous lactose and a suitable carbon source, thereby producing a fermentation broth comprising lacto-N-triose II, LNT or LNnT,
c) harvesting the fermentation broth comprising lacto-N-triose II, LNT or LNnT.

If no recombinant gene encoding a galactosyl transferase is present in the cell, the product is preferably lacto-N-triose II, and if a recombinant β-1,3- or a β-1,4-galactosyl transferase is also present in the cell, the product is preferably LNT or LNnT, respectively. Such cells and their culturing are disclosed in e.g. Priem et al. *Glycobiology* 12, 235 (2002), Gebus et al. *Carbohydr. Res.* 361, 83 (2012), Baumgärtner et al. *ChemBioChem* 15, 1896 (2014) and *Enzyme Microb. Technol.* 75-76, 37 (2015), WO 01/04341, WO 2014/153253, WO 2015/036138, WO 2015/197082 or WO 2016/008602.

The fermentation broth so-produced comprises the N-acetylglucosamine containing neutral oligosaccharide, such as lacto-N-triose II, LNT or LNnT, both in the producing cells and the culture medium. To harvest the intracellular oligosaccharide and thereby to raise the titre of the product, the method described above may further comprise an optional step d) of disrupting or permeabilizing the cells, e.g. by heating.

The fermentation broth that comprises the N-acetylglucosamine containing neutral oligosaccharide can be accompanied by other carbohydrate compounds. Typically, another carbohydrate compound is lactose which is used as acceptor in the fermentation process for making the N-acetylglucosamine containing neutral oligosaccharide and left unconverted. In addition, another accompanying carbohydrate compound can be a intermediary carbohydrate during the biosynthetic pathway to the desired N-acetylglucosamine containing neutral oligosaccharide, e.g. lacto-N-triose II in case of producing LNT or LNnT. Although their amounts can be substantially reduced in the fermentation broth before subjecting it to the separation/purification steps disclosed below, e.g. as disclosed in WO 2012/112777 or WO 2015/036138, it is not necessary to do so. The claimed methods, particularly their preferred embodiments, are suitable to separate an N-acetylglucosamine containing neutral oligosaccharide accompanied by carbohydrate compounds from non-carbohydrate contaminants, while the relative proportion of the carbohydrate compounds does not substantially change in the course of the claimed method. Therefore the purpose of the claimed method is a separation of an N-acetylglucosamine containing neutral oligosaccharide accompanied by carbohydrate compounds from non-carbohydrate contaminants in an aqueous medium from fermentation broth or enzymatic reaction milieu rather than the purification of the an N-acetylglucosamine containing neutral oligosaccharide from any other contaminants including accompanying carbohydrate compounds. N-acetylglucosamine containing neutral oligosaccharides, particularly N-acetylglucosamine containing neutral human milk oligosaccharides, are intended to be used for nutritional purposes, therefore the presence of accompanying carbohydrates besides the main N-acetylglucosamine containing neutral human milk oligosaccharide in the final nutritional composition is not adverse, or it can even be advantageous.

Accordingly, in one embodiment, wherein the N-acetylglucosamine containing neutral human milk oligosaccharide is LNT and produced by fermentation, the accompanying carbohydrates are mainly lactose (as acceptor employed in the fermentation and left unreacted), lacto-N-triose II (GlcNAcβ1-3Galβ1-4Glc, as intermediary carbohydrate in the biosynthetic pathway to LNT) and p-LNH II (Galβ1-3GlcNAcβ1-3Galβ1-3GlcNAcβ1-3Galβ1-4Glc, as overglycosylated LNT that has similar biological properties to LNT). In another embodiment, wherein the N-acetylglucosamine containing neutral human milk oligosaccharide is LNnT and produced by fermentation, the accompanying carbohydrates are mainly lactose (as acceptor employed in the fermentation and left unreacted), lacto-N-triose II (GlcNAcβ1-3Galβ1-4Glc, as intermediary carbohydrate in the biosynthetic pathway to LNnT) and p-LNnH (Galβ1-4GlcNAcβ1-3Galβ1-4GlcNAcβ1-3Galβ1-4Glc, as overglycosylated LNnT that has similar biological properties to LNnT). In another embodiment, wherein the N-acetylglucosamine containing neutral human milk oligosaccharide is lacto-N-triose II (GlcNAcβ1-3Galβ1-4Glc) and produced by fermentation, the accompanying carbohydrate is mainly lactose (as acceptor employed in the fermentation and left unreacted).

According to the invention, the fermentation broth is further subjected to a procedure of separation/purification of the N-acetylglucosamine containing neutral oligosaccharides from other non-carbohydrate compounds of the broth which is described below.

2.2 Separation of N-Acetylglucosamine Containing Neutral Oligosaccharides from the Fermentation Broth The invention relates to a method for separating an N-acetylglucosamine containing neutral oligosaccharide from other compounds present in a fermentation broth obtained by culturing a genetically modified microorganism capable of producing said N-acetylglucosamine containing neutral oligosaccharide from an internalized carbohydrate precursor.

The method comprises the following separation/purification steps in any order:
  i) ultrafiltration (UF),
  ii) nanofiltration (NF), and
  iii) treatment with an ion exchange resin, and/or chromatography on a neutral solid phase.

Preferably, the method does not comprise electrodialysis.

Advantageously, step i) is conducted before step ii). More advantageously, the step i) is conducted before any of the steps ii) and iii). Preferably, the method is performed in the order where step ii) follows step i) and step iii) follows step ii).

In one embodiment, the method comprises:
  ultrafiltration (UF) of the fermentation broth and collecting the ultrafiltration permeate (UFP),
  nanofiltration (NF) of the UFP and collecting the nanofiltration retentate (NFR),
  treatment of the NFR with an ion exchange resin, and collecting the resin eluate (RE), and
  chromatography of the RE.

In another embodiment, the method comprises:
  ultrafiltration (UF) of the fermentation broth and collecting the ultrafiltration permeate (UFP),
  nanofiltration (NF) of the UFP and collecting the nanofiltration retentate (NFR),
  chromatography of the NFR, and collecting the chromatography eluate (CE), and
  treatment of the CE with an ion exchange resin.

The method of the invention may comprise an active charcoal treatment after UF, NF, chromatography or ion exchange resin treatment.

In one embodiment, the method comprises:
  ultrafiltration (UF) of the fermentation broth and collecting the ultrafiltration permeate (UFP),
  nanofiltration (NF) of the UFP and collecting the nanofiltration retentate (NFR),
  activated charcoal treatment of the NFR, and collecting the charcoal eluate (CCE), and
  treatment of the CCE with an ion exchange resin.

Preferably, the method comprises:
  ultrafiltration (UF) of the fermentation broth and collecting the ultrafiltration permeate (UFP),
  nanofiltration (NF) of the UFP and collecting the nanofiltration retentate (NFR),
  activated charcoal treatment of the NFR, and collecting the charcoal eluate (CCE), and
  treatment of the CCE with a strong cation exchange resin in H$^+$-form and a weak anion exchange resin in free base form.

More preferably, the method comprises:
  ultrafiltration (UF) of the fermentation broth and collecting the ultrafiltration permeate (UFP),
  nanofiltration (NF) of the UFP and collecting the nanofiltration retentate (NFR), activated charcoal treatment of the NFR, and collecting the charcoal eluate (CCE), and treatment of the CCE with a strong cation exchange resin in H⁺-form and a weak anion exchange resin in free base form;

and a the method does not comprise electrodialysis.

In another embodiment, the method comprises:

ultrafiltration (UF) of the fermentation broth and collecting the ultrafiltration permeate (UFP), nanofiltration (NF) of the UFP and collecting the nanofiltration retentate (NFR), treatment of the NFR with an ion exchange resin, and collecting the resin eluate (RE), and activated charcoal treatment of the RE.

Preferably, the method comprises:

ultrafiltration (UF) of the fermentation broth and collecting the ultrafiltration permeate (UFP), nanofiltration (NF) of the UFP and collecting the nanofiltration retentate (NFR), treatment of the NFR with a strong cation exchange resin in H⁺-form and a weak anion exchange resin in free base form, and collecting the resin eluate (RE), and activated charcoal treatment of the RE.

More preferably, the method comprises:

ultrafiltration (UF) of the fermentation broth and collecting the ultrafiltration permeate (UFP), nanofiltration (NF) of the UFP and collecting the nanofiltration retentate (NFR), treatment of the NFR with a strong cation exchange resin in H⁺-form and a weak anion exchange resin in free base form, and and collecting the resin eluate (RE), and activated charcoal treatment of the RE;

and the method does not comprise electrodialysis.

Yet in another embodiment, the method comprises:

ultrafiltration (UF) of the fermentation broth and collecting the ultrafiltration permeate (UFP), nanofiltration (NF) of the UFP and collecting the nanofiltration retentate (NFR), chromatography of the NFR, and collecting the chromatography eluate (CE), and activated charcoal treatment of the CE.

Yet in another embodiment, the method comprises:

ultrafiltration (UF) of the fermentation broth and collecting the ultrafiltration permeate (UFP), nanofiltration (NF) of the UFP and collecting the nanofiltration retentate (NFR), activated charcoal treatment of the NFR and collecting the charcoal eluate (CCE), and chromatography of the CCE.

Yet in another embodiment, the method comprises:

ultrafiltration (UF) of the fermentation broth and collecting the ultrafiltration permeate (UFP), nanofiltration (NF) of the UFP and collecting the nanofiltration retentate (NFR), chromatography of the NFR, and collecting the chromatography eluate (CE), activated charcoal treatment of the CE, and collecting the charcoal eluate (CCE), and treatment of the CCE with an ion cation exchange resin.

Yet in another embodiment, the method comprises:

ultrafiltration (UF) of the fermentation broth and collecting the ultrafiltration permeate (UFP), nanofiltration (NF) of the UFP and collecting the nanofiltration retentate (NFR), chromatography of the NFR, and collecting the chromatography eluate (CE), treatment of the CE with an ion exchange resin, and collecting the resin eluate (RE), and activated charcoal treatment of the RE.

Yet in another embodiment, the method comprises:

ultrafiltration (UF) of the fermentation broth and collecting the ultrafiltration permeate (UFP), nanofiltration (NF) of the UFP and collecting the nanofiltration retentate (NFR), treatment of the NFR with an ion exchange resin, and collecting the resin eluate (RE)

chromatography of the RE, and collecting the chromatography eluate (CE), and activated charcoal treatment of the CE.

Yet in another embodiment, the method comprises:

ultrafiltration (UF) of the fermentation broth and collecting the ultrafiltration permeate (UFP), nanofiltration (NF) of the UFP and collecting the nanofiltration retentate (NFR), treatment of the NFR with an ion exchange resin, and collecting the resin eluate (RE)

activated charcoal treatment of the RE, and collecting the charcoal eluate (CCE), and chromatography of the CCE.

Yet in another embodiment, the method comprises:

ultrafiltration (UF) of the fermentation broth and collecting the ultrafiltration permeate (UFP), nanofiltration (NF) of the UFP and collecting the nanofiltration retentate (NFR), activated charcoal treatment of the NFR, and collecting the charcoal eluate (CCE), treatment of the CCE with an ion exchange resin, and collecting the resin eluate (RE), and chromatography of the RE.

Yet in another embodiment, the method comprises:

ultrafiltration (UF) of the fermentation broth and collecting the ultrafiltration permeate (UFP), nanofiltration (NF) of the UFP and collecting the nanofiltration retentate (NFR), activated charcoal treatment of the NFR, and collecting the charcoal eluate (CCE), chromatography of the CCE, and collecting the chromatography eluate (CE), and treatment of the CE with an ion exchange resin.

The method of the invention provides a solution highly enriched with the N-acetylglucosamine containing neutral oligosaccharide from which that oligosaccharide can be obtained in high yield and preferably with a satisfactory purity, such as one that meets the strict regulatory requirements for food applications.

2.2.1. Step i) of the Separation/Purification of the N-Acetylglucosamine Containing Neutral Oligosaccharide According to step i) of the method, the broth obtained from fermentation is subjected to ultrafiltration, preferably as a first step. The fermentation broth typically contains, besides the N-acetylglucosamine containing neutral oligosaccharides produced, the biomass of the cells of the used microorganism together with proteins, protein fragments, DNA, endotoxins, biogenic amines, inorganic salts, unreacted carbohydrate acceptors such as lactose, sugar-like by-products, monosaccharides, colorizing bodies, etc. The ultrafiltration step is to separate the biomass and, preferably, also high molecular weight suspended solids from the soluble components of the broth which pass through the ultrafiltration membrane in the permeate. This UF permeate (UFP) is an aqueous solution containing the produced N-acetylglucosamine containing neutral oligosaccharide.

Any conventional ultrafiltration membrane can be used having a molecular weight cut-off (MWCO) range between about 1 and about 500 kDa, such as 10-250, 50-100, 200-500, 100-250, 1-100, 1-50, 10-25, 1-5 kDa, or any other suitable sub-ranges. The membrane material can be a ceramic or made of a synthetic or natural polymer, e.g. polysulfone, polypropylene, cellulose acetate or polylactic acid. The ultrafiltration step can be applied in dead-end or cross-flow mode. This step i) may comprise more than one ultrafiltration step using membranes with different MWCO, e.g. using two ultrafiltration separations wherein the first membrane has a higher MWCO than that of the second membrane. This arrangement may provide a better separation efficacy of the higher molecular weight components of the broth. After this separation step the permeate contains materials that have a molecular weight lower than the MWCO of the second membrane, including the N-acetylglucosamine containing neutral oligosaccharide of interest.

In one embodiment, the fermentation broth is ultrafiltered using a membrane having a MWCO of 5-30 kDa, such as 10-25, 15 or 20 kDa.

2.2.2. Step ii) of the Separation/Purification of the N-Acetylglucosamine Containing Neutral Oligosaccharide Step ii) of the method comprises a nanofiltration step. Step ii) may follow step i) or step iii) (described below), preferably step i). This nanofiltration step may advantageously be used to concentrate the previously treated fermentation broth having the N-acetylglucosamine containing neutral oligosaccharide and/or to remove ions, mainly monovalent ions, and organic materials having a molecular weight lower than that of the N-acetylglucosamine containing neutral oligosaccharide, such as monosaccharides. The nanofiltration membrane has a MWCO that ensures the retention of the N-acetylglucosamine containing neutral oligosaccharide of interest, that is its MWCO is lower than that of the ultrafiltration membrane(s) used in step i), and around 25-50% of the molecular weight of the N-acetylglucosamine containing neutral oligosaccharide. In this regard the N-acetylglucosamine containing neutral oligosaccharide is accumulated in the NF retentate (NFR). The nanofiltration can be combined with diafiltration with water to remove, or to reduce the amount of, permeable salts such as monovalent ions more effectively.

In one embodiment, step ii) follows step i), that is the UF permeate obtained in step i) is nanofiltered without diafiltration, and the NF retentate containing the produced N-acetylglucosamine containing neutral oligosaccharide is collected and subjected to further separation step(s) of the method.

In one embodiment, step ii) follows step i), that is the UF permeate obtained in step i) is nanofiltered followed by diafiltration, and the NF retentate containing the produced N-acetylglucosamine containing neutral oligosaccharide is collected and subjected to further separation step(s) of the method.

2.2.3. Step iii) of the Separation/Purification of the N-Acetylglucosamine Containing Neutral Oligosaccharide The separation/purification method, as mentioned above, comprises a step (iii) which in different embodiments may be either treatment with an anion and/or a cation exchange resin or a chromatographic step on a neutral solid phase, or both later steps. These embodiments of step iii) are described in detail below.

2.2.3.1. Step iii): Treatment with an Ion Exchange Resin

In step iii), the aqueous solution of the N-acetylglucosamine containing neutral oligosaccharide from step i) or ii) may be further purified by means of an ion exchange resin. Salts, colour bodies and/or charged macromolecules can be removed by treatment with resin.

According to one embodiment, the ion exchange resin is an anion exchange resin, preferably a weakly basic anion exchange resin. In this step the negatively charged materials can be removed from the pre-treated solution as they bind to the resin. The aqueous solution of the N-acetylglucosamine containing neutral oligosaccharide is contacted with an anion exchange resin in any suitable manner which would allow the negatively charged materials to be adsorbed onto the anion exchange resin, and the N-acetylglucosamine containing neutral oligosaccharide to pass through. The resulting liquid, after contacting with the anion exchange resin, contains primarily water, cations and neutral carbohydrates like the carbohydrate acceptor previously added to the fermentation culture to be glycosylated, e.g. lactose (if still left after one or more previous purification steps).

According to another embodiment, the ion exchange resin is a cation exchange resin, preferably a strongly acidic cation exchange resin. In this step the positively charged materials can be removed from the pre-treated solution as they bind to the resin. The solution of the N-acetylglucosamine containing neutral oligosaccharide is contacted with the cation exchange resin in any suitable manner which would allow positively charged materials to be adsorbed onto the cation exchange resin, and the N-acetylglucosamine containing neutral oligosaccharide to pass through. The resulting liquid, after contacting with the cation exchange resin, contains the N-acetylglucosamine containing neutral oligosaccharide besides anions and neutral carbohydrates like the carbohydrate acceptor previously added to the fermentation culture to be glycosylated, e.g. lactose (if still left after one or more previous purification steps).

One of the ion exchange resin treatments disclosed above in step iii) may be sufficient to obtain the N-acetylglucosamine containing neutral oligosaccharide in a required purity. If necessary, both cation and anion exchange resin chromatography, in any order, can be applied.

When using an ion exchange resin, its degree of cross-linking can be chosen depending on the operating conditions of the ion exchange column. A highly crosslinked resin offers the advantage of durability and a high degree of mechanical integrity, however suffers from a decreased porosity and a drop off in mass-transfer. A low-crosslinked resin is more fragile and tends to swell by absorption of mobile phase. The particle size of the ion exchange resin is selected to allow an efficient flow of the eluent, while the charged materials are still effectively removed. A suitable flow rate may also be obtained by applying a negative pressure to the eluting end of the column or a positive pressure to the loading end of the column, and collecting the eluent. A combination of both positive and negative pressure may also be used. The ion exchange treatment can be carried out in a conventional manner, e.g. batch-wise or continuously.

Non-limiting examples of a suitable acidic cation exchange resin can be e.g. Amberlite IR100, Amberlite IR120, Amberlite FPC22, Dowex 50WX, Finex CS16GC, Finex CS13GC, Finex CS12GC, Finex CS11GC, Lewatit S, Diaion SK, Diaion UBK, Amberjet 1000, Amberjet 1200.

Non-limiting examples of a suitable basic anion exchange resin can be e.g. Amberlite IRA67, Amberlite IRA 96, Amberlite IRA743, Amberlite FPA53, Diaion CRB03, Diaion WA10, Dowex 66, Dowex Marathon, Lewatit MP64.

In a preferred embodiment, step iii) comprises a treatment with a cation exchange resin in $H^+$-form and an anion exchange resin in free base form. The cation exchange resin is preferably a strong exchanger, and the anion exchange resin is a weak exchanger. This particular arrangement, besides removing salts and charged molecules from the remaining culture medium, can physically adsorb proteins, DNA and colorizing/caramel bodies efficiently that were left in the culture medium.

The application of a weak basic anion exchanger in free base form (that is, wherein the resin's functional group is a primary, secondary or tertiary amine) is advantageous compared to that of a strong basic anion exchanger in $OH^-$-form. The strong basic exchanger has the ability, due to its strong basicity, to deprotonate the anomeric OH-group of an N-acetylglucosamine containing neutral oligosaccharide. This initiates rearrangement reactions of the N-acetylglucosamine containing neutral oligosaccharide and thus creates by-products, and/or a significant amount of N-acetylglucosamine containing neutral oligosaccharide is bound to the resin. Consequently, both events contribute to the reduction of the recovery yield of the N-acetylglucosamine containing neutral oligosaccharide.

Moreover, the application of a weak anion exchange resin in free base form directly after a strong cation exchange resin treatment in $H^+$-form has additional advantages compared to the prior art solution (EP-A-2896628) wherein the anion exchanger is strong and in salt form (e.g. $Cl^-$, $AcO^-$, $HCO_3^-$):
  it effectively neutralizes the acidic eluent collected from the cation exchanger therefore providing a neutral eluent without requiring an extra neutralizing step between the two ion exchanger treatments (EP-A-2896628 suggests to use NaOH-solution to neutralize the eluent from the cation exchanger),
  it does not introduce anions of the strong anion exchanger like $Cl^-$, $AcO^-$ or $HCO_3^-$ which would need to be removed later,
  the present setup efficiently lowers the conductivity of the resin load by almost two orders of magnitude and directly provides an eluent with low conductivity (below 200 µS/cm, preferably below 100 µS/cm, more preferably below 50 µS/cm), consequently with low salt electrolyte content (EP-A-2896628 suggests to use electrodialysis to obtain low conductivity).

The above mentioned remarkably low conductivity is reached for a solution comprising the N-acetylglucosamine containing neutral oligosaccharide that has a Brix of about 6-12 (wherein the Brix of the solution practically corresponds to the overall carbohydrate content in g/100 g solution).

In this regard step iii) consists of the treatment of the aqueous solution of the N-acetylglucosamine containing neutral oligosaccharide from step i) or ii) with a strong cation exchange resin in $H^+$-form directly followed by a treatment with a weak anion exchange resin in free base form.

Advantageously, the method for separating an N-acetylglucosamine containing neutral oligosaccharide from other, non-carbohydrate compounds present in a fermentation broth obtained by culturing a genetically modified microorganism capable of producing said N-acetylglucosamine containing neutral oligosaccharide from an internalized carbohydrate precursor, comprises the following separation/purification steps:
  i) ultrafiltration (UF),
  ii) nanofiltration (NF), and
  iii) treatment with an ion exchange resin,
  and does not comprise electrodialysis when step iii) consists of the treatment of the aqueous solution of the N-acetylglucosamine containing neutral oligosaccharide from step i) or ii) with a strong cation exchange resin in $H^+$-form directly followed by a treatment with a weak anion exchange resin in free base form.

2.2.3.2. Step iii): Chromatographic Purification on a Neutral Solid Phase

In step iii), the aqueous solution of the N-acetylglucosamine containing neutral oligosaccharide from step i) or ii) may be further purified by means of chromatography on a neutral solid phase.

The resulting aqueous medium after step i) and ii) may contain small amounts of other soluble hydrophobic impurities which should be removed. The impurities may be removed by subjecting this aqueous medium to a chromatography on a neutral solid phase, advantageously a reversed-phase chromatography. Thereby, contaminants that contain a hydrophobic moiety are adsorbed and consequently retained, due to hydrophobic interactions, with the hydrophobic ligands, such as alkyl or aryl side chains, of the gel matrix (resin) of the stationary phase, while the more hydrophilic N-acetylglucosamine containing neutral oligosaccharide does not bind onto the reversed-phase chromatographic medium and therefore is eluted with the aqueous medium, used as the mobile phase.

The reversed-phase chromatography can be carried out in a conventional manner. Preferably, a hydrophobic chromatographic medium is used that is selected from the group consisting of: reversed-phase silicas and organic polymers, especially copolymers of styrene or divinylbenzene and methacrylate polymer. The silicas are preferably derivatized with straight chain alkyl hydrocarbons ranging in length from C1 to C18 (C1, C4, C5 C8 and C18 being the most common) or other hydrophobic ligands (for example phenyl or cyano).

To the aqueous medium used as the mobile phase in the reversed-phase chromatography an organic solvent may be added to alter its polarity, thereby to enhance purification. Many organic solvents, preferably solvents miscible with water, can be used for this purpose, like lower alkanols, such as methanol, ethanol and isopropanol, or acetonitrile, or tetrahydrofuran, or acetone.

Also to enhance the purification of the N-acetylglucosamine containing neutral oligosaccharide, the pH of the aqueous medium is preferably adjusted to pH 3 to 8, such as 4 to 7, prior to reversed-phase chromatography. This is preferably accomplished in a conventional manner by addition, for example, of ammonium formate, ammonium acetate or ammonium hydrogen carbonate.

Also to enhance the purification of the N-acetylglucosamine containing neutral oligosaccharide, a salt is preferably dissolved in the aqueous medium prior to reversed-phase chromatography. The salt increases the hydrophobic interactions of the non-saccharide contaminants to increase their removal by the hydrophobic chromatographic medium. Salts that can be used include: $Na_2SO_4$, $K_2SO_4$, $(NH_4)_2SO_4$, NaCl, $NH_4Cl$, NaBr, NaSCN and $NaClO_4$.

The reversed-phase chromatography can otherwise be carried out in a conventional manner, e.g. batch-wise or continuously. The purification can be easily done by using a conventional chromatographic column or container of laboratory or industrial scale, in which the hydrophobic chromatographic medium can be either packed or suspended (e.g. as beads).

2.2.3.3. Step iii): Combination of Ion Exchange Treatment and Chromatography

Either the ion exchange resin treatment or the chromatographic purification disclosed above in step iii) may be sufficient to obtain the N-acetylglucosamine containing neutral oligosaccharide in a required purity. If necessary, both ion exchange exchange resin and reversed-phase chromatography, in any order, can be applied.

2.2.4. Optional Step(s)

The method of separation/purification of an N-acetylglucosamine containing neutral oligosaccharide of the invention from the fermentation broth may comprise one or more further optional steps, such as (A) activated charcoal treatment (preferably to decolorize the broth) and/or (B) providing the N-acetylglucosamine containing neutral oligosaccharide in isolated form.

2.2.4.1. Optional Step A: Active Charcoal Treatment

According to certain embodiments, the method of invention comprises the optional step of active charcoal treatment. The optional active charcoal treatment may follow any of step i), step ii) or step iii). The active charcoal treatment helps to remove colorizing agents and/or to reduce the amount of water soluble contaminants, such as salts, if required.

A carbohydrate substance like an N-acetylglucosamine containing neutral oligosaccharide of interest tends to be bound to the surface of charcoal particles from its aqueous solution, e.g. an aqueous solution obtained after on step i), step ii) or step iii). Similarly, the colorizing agents are also capable to be adsorbed to the charcoal. While the carbohydrates and colour giving materials are adsorbed, water soluble materials that are not or are more weakly bound to the charcoal can be eluted with water. By changing the eluent from water to aqueous ethanol, the adsorbed N-acetylglucosamine containing neutral oligosaccharide can easily be eluted and collected in a separate fraction. The adsorbed colour giving substances would still remain adsorbed on the charcoal, thus both decolourization and partial desalination can be achieved simultaneously in this optional step. However, due to the presence of organic solvent (ethanol) in the elution solvent the efficacy of decolorization is lower compared to the case when the elution is done with pure water (see below).

Under certain conditions, the N-acetylglucosamine containing neutral oligosaccharide is not, or at least not substantially, adsorbed to the charcoal particles and elution with water gives rise to an aqueous solution of the N-acetylglucosamine containing neutral oligosaccharide without a significant loss in its amount, while the colour giving substances remain adsorbed. In this case there is no need to use organic solvent such as ethanol for elution. It is a matter of routine skills to determine the conditions under which the N-acetylglucosamine containing neutral oligosaccharide would bind to the charcoal from its aqueous solution. For example, in one embodiment a more diluted solution of the N-acetylglucosamine containing neutral oligosaccharide or a higher amount of charcoal relative to the amount of the N-acetylglucosamine containing neutral oligosaccharide is used, in another embodiment a more concentrated solution of the N-acetylglucosamine containing neutral oligosaccharide and a lower amount of charcoal relative to the amount of the N-acetylglucosamine containing neutral oligosaccharide is applied.

The charcoal treatment can be conducted by adding charcoal powder to the aqueous solution of the N-acetylglucosamine containing neutral oligosaccharide under stirring, filtering off the charcoal, re-suspending in aqueous ethanol under stirring and separating the charcoal by filtration. In higher scale purification, the aqueous solution of N-acetylglucosamine containing neutral oligosaccharide after step i), step ii) or step iii) is preferably loaded to a column packed with charcoal, which may be a granulated charcoal or may optionally be mixed with celite, then the column is washed with the required eluent. The fractions containing the N-acetylglucosamine containing neutral oligosaccharide are collected. Residual ethanol may be removed from these fractions, if necessary, by e.g. evaporation, to give an aqueous solution of the N-acetylglucosamine containing neutral oligosaccharide.

In one preferred embodiment, the step of active charcoal treatment follows the nanofiltration step ii), and is applied on the NF retentate.

2.2.4.2. Optional Step B: Providing the N-Acetylglucosamine Containing Neutral Oligosaccharide in Isolated Form After the isolation/purification step i), step ii), step iii) and/or active charcoal treatment, the N-acetylglucosamine containing neutral oligosaccharide so-obtained can be provided in its solid form by means of spray-drying, freeze-drying or crystallization. Accordingly, the method of the invention may comprise one or more further steps of providing the N-acetylglucosamine containing neutral oligosaccharide in isolated, preferably, dried form, such as a step of spray-drying an aqueous solution of the N-acetylglucosamine containing neutral oligosaccharide obtained after step i), step ii), step iii) and/or active charcoal treatment; or a step of freeze-drying an aqueous solution of the N-acetylglucosamine containing neutral oligosaccharide obtained after step i), step ii), step iii) and/or active charcoal treatment; or a step of crystallising the N-acetylglucosamine containing neutral oligosaccharide obtained after step i), step ii), step iii) and/or active charcoal treatment. Alternatively, the N-acetylglucosamine containing neutral oligosaccharide isolated and purified by the above method may be provided in a form of a concentrated aqueous solution or syrup by removing water, e.g. by means of distillation, preferably vacuum distillation, or nanofiltration.

3. Method for Separating N-Acetylglucosamine Containing Neutral Oligosaccharide from Dissolved Inorganic and Organic Salts, Acids and Bases in an Aqueous Medium from a Fermentation or Enzymatic Process A possible way for producing N-acetylglucosamine containing neutral oligosaccharides is fermentation, which method has already been disclosed in 2.1. Alternatively, N-acetylglucosamine containing neutral oligosaccharides can be synthesized in a glycosyl transferase catalyzed reaction, wherein the glycosyl transferase is bound to the surface of a cell (see e.g. WO 95/02683). Moreover, enzymatic reactions in a cell-free medium involving glycosyl transferases, transglycosidase or a combination thereof (see e.g. Murata et al. *Glycoconj. J.* 16, 189 (1999)) are also suitable to prepare N-acetylglucosamine containing neutral oligosaccharides. Whatever method is employed, the reaction milieu contains salts (buffers) to regulate the pH for ensuring the optimal condition for glycosyl transferases/transglycosidases and/or micronutrients for cells. As a consequence of the complex reaction milieu the reaction medium, after the N-acetylglucosamine containing neutral oligosaccharides having been produced, often contains water soluble charged contaminant and impurities (e.g. peptide residues, organic acids and bases) besides the salts, which are difficult to separate in a conventional manner from the oligosaccharides.

To solve the above problem efficiently, in another aspect, the invention relates to the separation of an N-acetylglucosamine containing neutral oligosaccharide from dissolved inorganic and organic salts, acids and bases in an aqueous medium from a fermentation or enzymatic process, comprising the step of treating said aqueous medium with a strong cation exchange resin in H$^+$-form and a weak anion exchange resin in free base form.

This particular arrangement, besides removing salts and charged molecules from the remaining culture medium, can physically adsorb proteins, DNA and colorizing/caramel bodies efficiently that were left in the culture medium.

The application of a weak basic anion exchanger in free base form is advantageous compared to that of a strong basic anion exchanger in OH$^-$-form. The strong basic exchanger has the ability, due to its strong basicity, to deprotonate the anomeric OH-group of an N-acetylglucosamine containing neutral oligosaccharide. This initiates rearrangement reactions of the N-acetylglucosamine containing neutral oligosaccharide and thus creates by-products, and/or a significant amount of N-acetylglucosamine containing neutral oligosaccharide is bound to the resin. As a consequence, both events contribute to the reduction of the recovery yield of the N-acetylglucosamine containing neutral oligosaccharide.

Moreover, the application of a weak anion exchange resin in free base form directly after a strong cation exchange resin treatment in H$^+$-form has additional advantages compared to the prior art solution (EP-A-2896628) wherein the anion exchanger is strong and in salt form (e.g. Cl$^-$, AcO$^-$, HCO$_3^-$):

it effectively neutralizes the acidic eluent collected from the cation exchanger therefore providing a neutral eluent without requiring an extra neutralizing step between the two ion exchanger treatments (EP-A-2896628 suggests to use NaOH-solution to neutralize the eluent from the cation exchanger), it does not introduce anions of the strong anion exchanger like Cl$^-$, AcO$^-$ or HCO$_3^-$ which would need to be removed later, the present setup efficiently lowers the conductivity of the resin load by almost two orders of magnitude and directly provides an eluent with low conductivity (below 200 µS/cm, preferably below 100 µS/cm, more preferably below 50 µS/cm), consequently with low salt electrolyte content (EP-A-2896628 suggests to use electrodialysis to obtain low conductivity).

The above mentioned remarkably low conductivity is reached for a solution comprising the N-acetylglucosamine containing neutral oligosaccharide that has a Brix of about 6-12 (wherein the Brix of the solution practically corresponds to the overall carbohydrate content in g/100 g solution).

In this regard the method comprises the treatment of the aqueous medium from a fermentation or enzymatic process that contains the N-acetylglucosamine containing neutral oligosaccharide with a strong cation exchange resin in H$^+$-form directly followed by a treatment with a weak anion exchange resin in free base form.

Preferably, the method does not comprise electrodialysis after the ion exchange resin treatment.

Also preferably, the method does not comprise retreating the obtained purified solution of the N-acetylglucosamine containing neutral oligosaccharide with an ion exchange resin.

An aqueous medium from a fermentation or enzymatic process that comprises an N-acetylglucosamine containing neutral oligosaccharide and dissolved inorganic and organic salts, acids and bases can be pretreated before applying the ion exchange resin treatment as disclosed above. The pretreatment step comprises a conventional clarification step for removing cells, cells fragments, proteins, protein fragments and insoluble materials directly after the fermentation or enzymatic production of the N-acetylglucosamine containing neutral oligosaccharide. The purpose of the pre-treatment step is to provide a substantially clear and particle-free solution that can be applied as feed solution for ion exchange columns. Preferably, the pre-treatment comprises ultrafiltration and nanofiltration as disclosed in 2.2.1 and 2.2.2, respectively.

Accordingly, in a certain embodiment of the method for separating of an N-acetylglucosamine containing neutral oligosaccharide from dissolved inorganic and organic salts, acids and bases in an aqueous medium from a fermentation or enzymatic process, that comprises the step of treating said aqueous medium with a strong cation exchange resin in H$^+$-form and a weak anion exchange resin in free base form, this step is preceded by ultrafiltration and nanofiltration. In a preferred embodiment the fermentation broth or the enzymatic reaction medium comprising the N-acetylglucosamine containing neutral oligosaccharide produced is ultrafiltered to separate the biomass and/or high molecular weight suspended solids from soluble components of the broth or the enzymatic reaction medium and thus to obtain an UF permeate that contains the N-acetylglucosamine containing neutral oligosaccharide, which UF permeate is nanofiltered to obtain the NF retentate that contains the N-acetylglucosamine containing neutral oligosaccharide, and which NF retentate is then subjected to ion exchange treatment as disclosed above.

Also in a certain embodiment, the method comprises the optional step of active charcoal treatment. The optional active charcoal treatment may follow UF, NF or the ion exchange treatment. The active charcoal treatment helps to remove colorizing agents, as disclosed in 2.2.4.1. In one particular embodiment, the step of active charcoal treatment follows the nanofiltration step and is applied on the NF retentate. In other particular embodiment, the step of active charcoal treatment follows the ion exchange treatment and is applied on the resin eluate.

EXAMPLES

Example 1

Fermentative Production of LNnT

A strain is constructed from *Escherichia coli* K12 strain DH1, obtained from the Deutsche Sammlung von Mikroorganismen (reference DSM 5346). The following genes are deleted: nadC, lacZ, nanKETA, lacA, lad, melA, wcaJ and mdoH, while maintaining genes involved in the UDP-GlcNAc and UDP-Gal biosynthesis. The strain contains a *N. meningitidis* lgtA gene for β-1,3-N-acetylglucosaminyl transferase integrated in the genome of the strain and plasmid carrying *Helicobacter pylori* galT gene for β-1,4-galactosyl transferase and the native regulatory and coding sequence of nadC.

Glucose, glycerol and lactose are each sterilized at 120° C.

Fermentation parameters for a 2 l fermenter: 0.6 l of aqueous minimal culture medium (Samain et al. *J. Biotechnol.* 72, 33 (1999) is placed in a fermenter, the temperature is kept at 28° C. and the pH is regulated at 6.8 with 28% NH$_4$OH. The inoculum of the strain is in a defined minimal medium (20 ml) supplemented with trace minerals. The exponential growth phase starts with the inoculation and stops when the glucose carbon source, initially added to the aqueous minimal culture medium, is exhausted. A feeding solution of glycerol (750 g/l) is added to the culture medium with a feed rate of 7 ml/h. Lactose is added in two portions: 75 g in 150 ml of water after 10 hours, then 35 g in 70 ml of water after 50 hours. The fermentation lasts for about 90-100 hours and produces a final aqueous culture medium containing LNnT accompanied by LNTri II, pLNnH and remaining lactose (LNnT titre: 40-45 g/l).

The fermentation was realized with 400 l of starting aqueous minimal culture medium.

Example 2

Fermentative Production of LNT

A strain is constructed from *Escherichia coli* K12 strain DH1, obtained from the Deutsche Sammlung von Mikroorganismen (reference DSM 5346). The following genes are deleted: nadC, lacZ, nanKETA, lacA, lacI, melA, wcaJ and mdoH, while maintaining genes involved in the UDP-GlcNAc and UDP-Gal biosynthesis. The strain contains a *N. meningitidis* lgtA gene for β-1,3-N-acetylglucosaminyl transferase integrated in the genome of the strain and plasmid carrying *Helicobacter pylori* ATCC 43504 galTK gene for β-1,3-galactosyl transferase and the native regulatory and coding sequence of nadC.

Glucose and lactose are each sterilized at 120° C.

Fermentation parameters for a 2 l fermenter: 0.6 l of aqueous minimal culture medium (Samain et al. *J. Biotechnol.* 72, 33 (1999) is placed in a fermenter, the temperature is kept at 28° C. and the pH is regulated at 6.8 with 28% NH$_4$OH. The inoculum of the strain is in a defined minimal medium (20 ml) supplemented with trace minerals. The exponential growth phase starts with the inoculation and stops when the glucose carbon source, initially added to the aqueous culture medium, is exhausted. A feeding solution of glucose (750 g/l) is added to the culture medium with a feed rate of 7 ml/h. Lactose is added in two portions: 80 g in 160 ml water after 1 hour, then 40 g in 80 ml of water after 42 hours. The fermentation lasts for about 85-95 hours and produces a final aqueous culture medium containing LNT accompanied by LNTri II, pLNH II and remaining lactose (LNT titre: 40-45 g/l).

The fermentation was realized with 400 l of starting aqueous minimal culture medium.

Example 3

Pre-Treatment of Fermentation Batches Before Ion Exchange Treatment

A fermentation broth containing LNT or LNnT (350-510 l) is ultrafiltered (15 kDa, e.g. Novasep BE) at 60-65° C. to collect the permeate with a concentration factor of about 1.5-2. The UF retentate is then washed with purified water (1.5-2.5-fold volumes relative to the initial broth volume ultrafiltered) and the suspension is filtered through the same membrane to collect a washing filtrate so that the combined volume of the UFP and washing filtrate is 1000-1100 l. The combined UF permeate and washing filtrate is nanofiltered applying a 150-300 Da membrane at 20-22 bars and 45° C. until the retentate had a total carbohydrate concentration of 130-220 g/kg (for LNnT) or 200-250 g/kg (for LNT). The amounts of accompanying carbohydrates in the LNnT solution (relative to the mass of LNnT): lactose 6-15%, lacto-N-triose II 0.7-1.6%, pLNnH 9-15%; the amounts of accompanying carbohydrates in the LNT solution (relative to the mass of LNT): lactose 8-16%, lacto-N-triose II 8.1-13.2%, pLNH II 2.2-3.6%.

Example 4

Ion Exchange Treatment of an LNnT Feed

NF retentate containing LNnT (23.3 kg in 248 kg of solution) was loaded to an agitated vessel through a 0.2 μm filter. Powdered active charcoal (10 kg, Acticarbon L3 S) was added and the suspension was stirred for 1 hour at 8±2° C. The active charcoal was then filtered over a horizontal plate filter by recirculating the solution until it became clear. The solution was transferred to a clean vessel and the charcoal was washed with 2×75 l of distilled water to give a combined solution (420 l) having a conductivity of 1.79 mS/cm (LNnT contr: 48.6 g/kg).

A column of a strong acidic cation exchange resin (Amberlite FPC22H, 120 l) and a column of a weakly basic anion exchange resin in base form (Amberlite FPA53, 110 l) were coupled together so that the bottom of the acidic column was connected to the top of the basic column. Before use, the columns were washed with distilled water until a pH of about 6 and a conductivity of 20 μS/cm were reached at the outlet of the basic column.

The above obtained charcoal eluate was loaded to the top of the acidic column. The elution was continued with distilled water. The collection of fractions was started when the Brix value of the eluate from the anion exchanger column raised from 0 and stopped when it reduced back to 0.5. A solution containing LNnT (20 kg in 460 l) was collected with a conductivity of 29 μS/cm. The solution was then concentrated to a solution that had a Brix of 29.8 (LNnT concrt: 184 g/kg)

Example 5

Ion Exchange Treatment of an LNT Feed

A column of a strong acidic cation exchange resin (Amberlite FPC22H, 125 l) and a column of a weakly basic anion exchange resin in base form (Amberlite FPA53, 120 l) were coupled together so that the bottom of the acidic column was connected to the top of the basic column. Before use, the columns were washed with distilled water until a pH of about 6 and a conductivity of 20 μS/cm were reached at the outlet of the basic column.

NF retentate containing LNT (35.8 kg in 178 l of solution, conductivity: 3.3 mS/cm) was loaded to the top of the acidic column. The elution was continued with distilled water. The collection of fractions was started when the Brix value of the eluate from the anion exchanger column raised from 0 and stopped when it reduced back to 0.5. A solution containing LNT (33.8 kg in 387 l, Brix: 12) was collected with a conductivity of 38 μS/cm.

The above ion exchange eluate was loaded to an agitated vessel through a 0.2 μm filter. Powdered active charcoal (8.44 kg, Acticarbon L3S) was added and the suspension was stirred for 1 hour at 8±2° C. The active charcoal was then filtered over a horizontal plate filter by recirculating the solution until it became clear. The solution was transferred to a clean vessel and the charcoal was washed with 2×50 l of distilled water to give a combined LNT solution (32.2 kg in 489 l).

The invention claimed is:

1. A method for separating lacto-N-triose II, lacto-N-tetraose, or lacto-n-neotetraose from dissolved inorganic and organic salts, acids and bases in an aqueous medium from a fermentation or enzymatic process, comprising the ordered steps of:
   applying ultrafiltration to said aqueous medium to form an ultrafiltration permeate;
   applying nanofiltration to the ultrafiltration permeate to form a nanofiltrate retentate;
   treating the nanofiltration retentate with a strong cation exchange resin in $H^+$-form and then immediately with a weak anion exchange resin in free base form to form a low conductive solution of lacto-N-triose II, lacto-N-tetraose, or lacto-n-neotetraose, wherein the low conductive solution has a conductivity one to two orders of magnitude lower than the conductivity of said aqueous medium.

2. The method according to claim 1 which does not comprise electrodialysis.

3. The method according to claim 1, wherein the lacto-N-triose II, lacto-N-tetraose, or lacto-n-neotetraose is produced by culturing a genetically modified microorganism capable of producing said oligosaccharide from an internalized lactose.

4. The method according claim 3, wherein the genetically modified microorganism is an *E. coli* of $LacY^+$ phenotype.

5. The method according to claim 4, wherein the *E. coli* comprises a recombinant β1,3-N-acetylglucosaminyl transferase.

6. The method according to claim 1, wherein the low conductive solution has a conductivity below 200 μS/cm.

7. The method according to claim 1, wherein the low conductive solution has a conductivity below 50 μS/cm.

8. The method according to claim 1, wherein the low conductive solution has a Brix of about 6-12.

* * * * *